United States Patent [19]

Packard et al.

[11] Patent Number: 4,841,976
[45] Date of Patent: Jun. 27, 1989

[54] STEERABLE CATHETER GUIDE

[75] Inventors: Brian M. Packard, Delano; Mark A. Rydell, Golden Valley, both of Minn.

[73] Assignee: Schneider-Shiley (USA) Inc., Minneapolis, Minn.

[21] Appl. No.: 134,103

[22] Filed: Dec. 17, 1987

[51] Int. Cl.$^4$ ............................................. A61B 6/00
[52] U.S. Cl. .................................... 128/657; 128/772; 604/164; 604/280
[58] Field of Search ............... 128/656, 657, 658, 772; 604/95, 164, 170, 280, 281, 282; 156/294

[56] References Cited

U.S. PATENT DOCUMENTS

| | | | |
|---|---|---|---|
| 3,625,200 | 12/1971 | Muller | 128/772 |
| 3,841,308 | 10/1974 | Tate | 128/772 |
| 4,001,491 | 1/1977 | Bauer | 156/294 |
| 4,456,017 | 6/1984 | Miles | 604/95 |
| 4,504,268 | 3/1985 | Herlitze | 604/165 |
| 4,525,157 | 6/1985 | Vaillancourt | 604/165 |
| 4,538,622 | 9/1985 | Samson et al. | 128/657 |
| 4,545,390 | 10/1985 | Leary | 128/772 |
| 4,548,206 | 10/1985 | Osborne | 128/772 |
| 4,634,432 | 1/1987 | Kocak | 604/282 |

Primary Examiner—Max Hindenburg
Assistant Examiner—Randy Citrin
Attorney, Agent, or Firm—Orrin M. Haugen; Thomas J. Nikolai; Frederick W. Niebuhr

[57] ABSTRACT

A steerable catheter guide comprised of an outer tube and an inner member surrounded by and rotatable with respect to said outer tube is disclosed. The steerable catheter guide also includes a formable member bonded to said inner member and said outer tube in the area of their respective distal ends. This design causes any rotation of the inner member with respect to the outer member to impart a torque directly to the distal end of the guide making steering much easier and less erratic.

7 Claims, 1 Drawing Sheet

STEERABLE CATHETER GUIDE

BACKGROUND OF THE INVENTION

The present invention relates to an improved guide member for use when inserting a catheter into a vein or artery. More specifically, the present invention is directed toward an improved steerable guide member having an inner member which is rotatable with respect to a surrounding outer member over a major portion of the overall length of the guide member and is attached at its distal end to the outer member and to a formable tip member.

In recent years, many advances have been made in the catheter art and, in particular, the art associated with angioplasty catheters used in treating cardiovascular disease. However, problems have remained in the characteristics of the means employed for guiding such catheters through blood vessels.

Prior art guides are typically comprised of a tightly wound helical coil surrounding a single strand core wire where the two are welded together at the proximal and distal ends. Such guide means are advanced through an artery, for example, by first manually forming the wire at its distal tip, inserting the guide wire into the catheter, and then advancing the guide wire and catheter through the vessel while rotating its proximal end in an attempt to steer the formed distal end. However, such prior art guides have proven to be less than optimum in their design as far as the ability to transfer torque applied at the proximal end thereof to the distal tip to effect steering thereof. The physician must grasp the proximal end of the guide and attempt to rotate it as a unit, either within a blood vessel or within the lumen of a guide catheter. The substantial contact between the guide wire and the blood vessel or guide catheter presents frictional forces which must be overcome. As a result, the movement of the formed distal end portion of the guide wire tends to be somewhat erratic and unpredictable. Moreover, the contour of the wound coils results in a guide wire having a rough surface which is inclined to be more thrombogenic than a smooth surface.

Another type of guide which has been used is a polymer coated wire strand. Applying a torque to its proximal end causes the entire wire to rotate. However, this design is considered to be less advantageous because the tip cannot be bent or formed. Further, the coefficient of friction between this guide and the vascular wall surfaces makes the guide difficult to rotate and steer through the blood vessel.

A third catheter guide design which has gained some attention incorporates a core wire coated with a polymer which terminates approximately five inches from the guide's distal tip. A tightly wound helical coil covers the last five inches or so of the core wire. This design, however, still suffers from the problem that torque can only be transferred to the tip by rotating the entire guide wire thus increasing friction. Further, the flexibility of the shaft cannot readily be varied in this design.

SUMMARY OF THE INVENTION

The catheter guide member of the present invention includes an outer tube which surrounds an inner tube or solid wire with a slight clearance therebetween. The inner tube or wire can thus be rotated within the outer tube. The materials used to construct the inner tube or solid wire and the outer tube are selected to provide a low coefficient of friction. Secured to the distal end of the inner tube or wire and projecting therebeyond is a forming wire which can be bent to yield a desired arc to the distal tip portion of the guide. This forming wire is surrounded by the distal end portion of the outer tube and bonded to it by an acceptable adhesive. Thus, the design of the present invention permits torque to be readily transferred to the guide's distal tip by rotation of the inner tube or wire from its proximal end. As a result, the guide member of the present invention is much easier to steer through a blood vessel than those designs heretofor known in the art.

While a variety of materials can be used for the respective parts, in the preferred embodiment, the outer tube may be made of tetrafluoroethylene plastic sold under the trademark Teflon ® and the inner tube may be made of stainless steel hypodermic stock. Further, to ensure proper bonding of the forming wire which projects from the distal end of the inner tube with the outer tube in the area of a the guide's distal tip, that portion of the outer tube is preferably splined. This is necessitated by the fact that there are many acceptable adhesives which will bond to the wire, but, because of the smoothness and low friction coefficient of Teflon plastic, will not bond to it. Only when the inner surface of the Teflon tube is splined or made irregular in shape, will proper bonding between the wire and the outer tube occur.

The above-described configuration of the preferred embodiment yields a very low coefficient of friction between the outer tube and the blood vessel wall for ease of entry. Similarly, there is a very low coefficient of friction between the outer tube and the inner tube at all points except in the area of the tip where the two are bonded together. This construction permits torque to be transferred from the guide's proximal end directly to the formed tip, thus facilitating the steering of the tip into a desired vascular branch. In that the outer tube is very smooth and made from nylon, it is less thrombogenic than some prior art helical coil designs.

OBJECTS

One object of the present invention is to provide a catheter guide which is easily and atraumatically inserted through blood vessels.

A second object of the present invention is to provide such a catheter guide member having an outer tube, an inner tube or solid wire having a gripping member on its proximal end and rotatable within the outer tube, said inner tube or wire having an attached or integrally constructed formable tip.

A third object is to provide a catheter guide member in accordance with the foregoing objectives and having a low coefficient of friction between said inner tube or wire and said outer tube, and between guide member and catheter.

A fourth object is to provide a catheter guide in accordance with the foregoing objectives and having a formable metal wire associated with the distal end of said inner wire or tube; a splined section at the end of said outer tube which surrounds at least a portion of said wire, and suitable material to bond said wire to said outer tube.

These and other objects will become more readily apparent from a thorough reading of the detailed description of the invention in view of the drawings and the appended claims.

DETAILED DESCRIPTION OF THE PREFERRED EMBODIMENT

Figure 1:
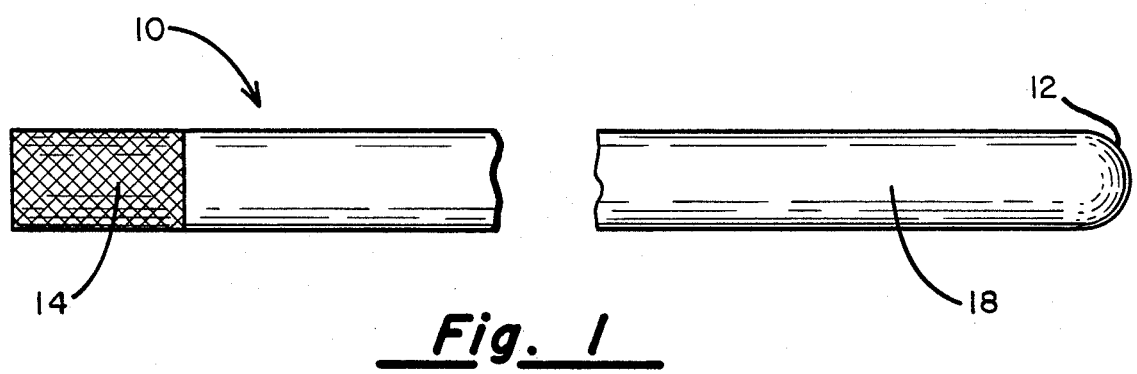
FIG. 1 is a side view of the catheter guide of the present invention.

FIG. 1 shows the outer shape of the guide member 10. The guide is sized so that it will be of sufficient length and outer diameter to be readily advanced through blood vessels until its distal end 12 reaches a desired location within the vascular system. It is also sized so that the guide 10 can be received within the guide lumen of a catheter such as an angioplasty balloon catheter (not shown) with which it is to be used. Also shown in FIG. 1 is a knurled handle member 14 which is affixed to the proximal end of the assembly and which can be rotated to apply a desired torque to the distal end 12.

Figure 2:
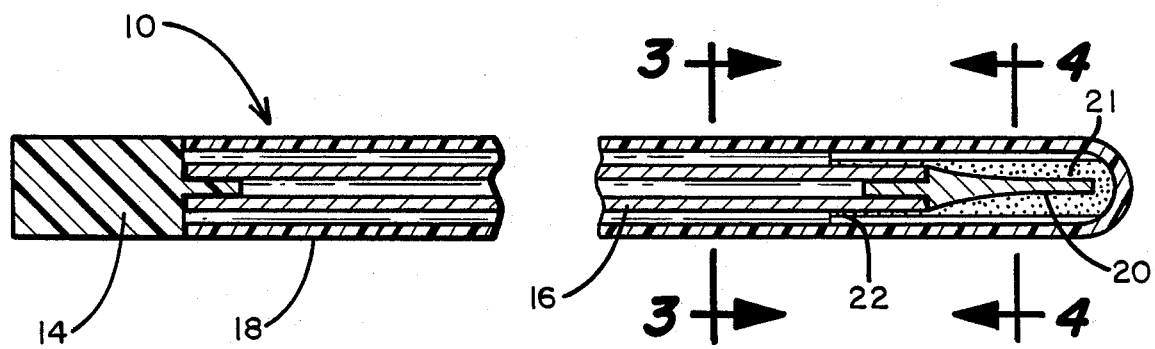
FIG. 2 is a cross-sectional side view of the catheter guide.
Figure 3:
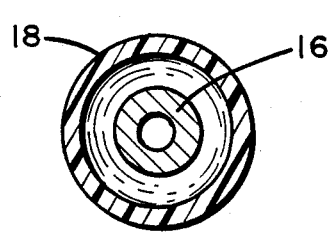
FIG. 3 is a cross-section of the catheter guide through line 3—3 in FIG. 1.
Figure 4:
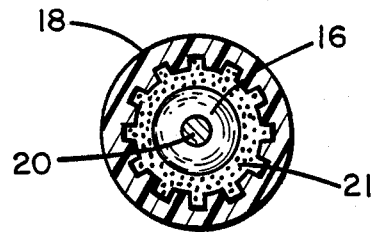
FIG. 4 is a cross-section through line 4—4 in FIG. 1.

FIGS. 2-4 show the internal construction of the catheter guide 10. The guide 10 is seen to include an inner tube 16, an outer tube 18, and a formable member 20 which is typically a wire having a memory property. It is not essential to the invention that the member 16 be tubular, but instead, may comprise a long, thin flexible solid wire.

In the preferred embodiment, the inner member 16 is tubular in form and may be constructed of stainless steel such as used in forming hypodermic needles and the outer tube 18 may be made of Teflon plastic or some other suitable polymer to yield a low coefficient of friction between the exterior wall of tube 16 and the interior wall of tube 18 and a smooth, non-thrombogenic exterior surface. Making the outer tube 18 of Teflon also yields a low coefficient of friction between the guide and any adjoining blood vessel or catheter wall when being used. Similar low coefficients of friction can be obtained if a material other than Teflon is used for the outer tube 18 by coating the parts with a suitable hydrophilic polymer which becomes slippery when wetted.

An important feature of the present invention is the inclusion of a formable member 20 and its interrelationship with the other components of the design. As best shown in FIG. 2, member 20 is attached to and projects outwardly beyond the distal end of inner tube 16 and may be tapered along its length as illustrated. A secure attachment between tube 16 and member 20 can be achieved through the use of an appropriate adhesive or by crimping the tube 16 to the member 20. Where the inner member 16 is a solid wire rather than a tube, it may include an integrally formed formable member on its distal end.

The purpose of member 20 is to provide a means by which the distal end 12 of the guide 10 can be formed so that it can be readily steered through blood vessels by manipulation of the handle member 14 at the proximal end of the guide member. Thus, it is important that the member 20 be stiff yet sufficiently flexible and able to retain a desired shape. The use of a radiopaque material for the forming member also proves expedient when fluroscopic techniques are used to view the inserting of the guide member.

Member 20 and the distal end portion of the center tube 16 is also secured to the outer tube 18. The manner in which this is achieved is best shown in FIGS. 2 and 4. As shown in FIG. 4 in the preferred embodiment, the distal end of the outer tube 18 is irregular in shape, creating a spline. An adhesive or moldable plastic 21 is then inserted into the gap 22 between member 20 and the splined portion of outer tube 18. Adhesives or moldable plastics which bond well to the material of the member 20 are to be selected because, when such materials set up, they will mechanically coact with the splines of the outer tube 18 to create a positive coupling irrespective of the low coefficient of friction of Teflon material. With this construction, upon rotation of the hub 14 connected to the inner tube 16, tube 16 will rotate within the outer tube 18 and torque necessary for steering the distal end of the guide 10 is directly applied to the distal end portion of the guide member 10 only cause the distal tip end occupied by forming member 20 and the splined portion of outer tube 18 to rotate.

Given the structure described above, use of the guide member is relatively straight-forward and easily understood. When in use, the distal end of guide member 10 is manually bent by the surgeon to a desired angle or curvature and inserted through a working catheter until the distal end of the guide projects a short distance beyond the distal end of the working catheter. Such working catheters have a lumen running their entire length. This lumen is designed to receive the guide member 10. A conventional introducer is used to insert the guide member 10 and catheter into the blood vessel. The guide member and catheter are then advanced through the blood vessel until the distal end 21 of the guide member reaches a desired location, such as a vascular branch. The guide member is then steered as it is further advanced by manipulating the handle 14 while holding the outer tube 18 of the guide member 10 stationary. The catheter travels with the guide member as the two are advanced. Once the guide member 10 has been fully advanced into the desired position within the vessel, the working catheter (such as one designed for coronary angioplasty) is advanced further over the guide member until the working portion of the catheter reaches the treatment site. The guide member 10 can then be withdrawn, making the catheter's lumen available for other uses, such as the profusion of blood or other fluids.

With no limitation intended, the outer diameter of the inner tube 16 may be in the range from 0.008 to 0.038 mills and may have a wall thickness of 0.005 mills which, when formed from stainless steel, provides sufficient flexure to the overall guide member 10 while effectively transferring torque to the distal end of the assembly when the knob or handle 14 is rotated. Where a solid wire core is used instead of tubular stock for the member 16, it may comprise a stainless strand having a diameter in the range of form 0.008 inches to 0.038 inches.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to equipment details and operating procedures, can be accomplished without departing from the scope of the invention itself.

What is claimed is:

1. A steerable catheter guide member for facilitating the insertion of a catheter having a lumen surrounded by a catheter wall into a blood vessel, comprising:
   (a) an elongated, flexible inner member having a proximal end and a distal end having a flexible formable distal tip portion;
   (b) an elongated, flexible outer tube having a proximal end and a distal end, said outer tube surrounding said inner member with a predetermined clearance therebetween over a majority of the length of said inner member, the outside diameter of said outer tube being of a size receivable in and movable through the vascular system of the patient;
   (c) means at the proximal end of said inner member for facilitating rotation of said inner member with respect to said outer tube; and
   (d) means for bonding said formable distal tip portion on said inner member to said outer tube near said distal end of said outer tube.

2. The catheter guide member of claim 1 wherein said inner member is tubular and said formable distal tip portion is attached to said distal end of said inner member.

3. The catheter guide member of claim 2 wherein said inner member is made of stainless steel.

4. The catheter guide member of claim 1 wherein said outer tube is made of tetrafluoroethylene plastic.

5. The catheter guide member of claim 4 wherein said outer tube has a non-circular internal cross-section near its distal end in the zone surrounding said formable tip portion.

6. The catheter guide member of claim 1 wherein said outer tube is coated with a hydrophilic polymer.

7. The catheter guide of claim 1 wherein said means for bonding said formable tip portion to said outer tube includes an internally splined portion on said outer tube in the location surrounding said formable tip portion; and an adhesive filling the space between said formable tip and said splined portion of said outer tube.

* * * * *